United States Patent [19]

Baskin et al.

[11] Patent Number: 4,859,674

[45] Date of Patent: Aug. 22, 1989

[54] PYRAZINE IN PREVENTION AND TREATMENT OF STROKES

[75] Inventors: David Baskin, Houston; Dominic M. K. Lam, The Woodlands, both of Tex.

[73] Assignee: Houston Biotechnology Incorporated, The Woodlands, Tex.

[21] Appl. No.: 228,827

[22] Filed: Aug. 3, 1988

Related U.S. Application Data

[63] Continuation of Ser. No. 62,109, Jun. 12, 1987, abandoned.

[51] Int. Cl.$^4$ ............................................ A61K 31/495
[52] U.S. Cl. ...................................... 514/255; 514/824
[58] Field of Search ............... 544/3367; 514/255, 824

[56] References Cited

PUBLICATIONS

Conn's Current Therapy; R. E. Riskel (ed) W. B. Saunders Co., 1986.

Guo-Shi-Kui, Chen Kei-Jii Qian Zhen-Hwai, Weng Wei-Liang, Qian Mu-Ying, Tetramethylpyrazine in the Treatment of Cardiovascular and Cerebrovascular Diseases, *Planta Medica* 47:89 (1983).

J. A. O. Ojewole, Effects of Tetramethylpyrazine on Isolated Atria of the Guinea-Pig, (1981) 42:223-228.

J. A. O. Ojewole, Blockade of Adrenergic and Cholinergic Transmissions by Tetramethylpyrazine, (1981) 43:1-10.

Baskin et al., Naloxone Reversal of Ischaemic Neurological Deficits in Man, (Aug. 8, 1981) pp. 272-275.

Baskin et al., Naloxone Reversal and Morphine Exacerbation of Neurologic Deficits Secondary to Focal Cerebral Ischemia in Baboons, (1984) 290:289-296.

Dai et al., Coronary and Systemic Hemodynamic Effects of Tetramethylpyrazine in the Dog, (1985) 7:841-849.

Chang et al., Pharmacology and Applications of Chinese Materia Medica, (1986) pp. 131-140.

*Primary Examiner*—Stanley J. Friedman
*Attorney, Agent, or Firm*—Bertram I. Rowland

[57] ABSTRACT

Neurologic dysfunction resulting from stroke is diminished by administering to a patient an effective amount of a tetra-substituted pyrazine over a relatively continuous regimen. Conveniently, an initial bolus is administered to bring the level of the drug up to a pre-determined blood level, followed by continuous infusion employing a pump or by continuous intravenous infusion.

6 Claims, No Drawings

PYRAZINE IN PREVENTION AND TREATMENT OF STROKES

This is a continuation of application Ser. No. 062,109 filed June 12, 1987, now abandoned.

TECHNICAL FIELD

The field concerns the use of drugs, particularly tetraalkylpyrazines to reduce ischemic defects and/or improve survival associated with stroke.

BACKGROUND

Stroke is associated with the blockage of blood flow to one or more sites of the brain. If the period of blockage is long enough, the stroke leads to cell death. Usually, the initial zone of cell death is relatively small and if the stroke were limited to that region, the effects might be relatively mild. However, the death of the cells leads to an inflow of fluid to the region, the degradation of the cells, and the release of intracellular contents. The effect is that the region of cell death becomes enlarged, so as to greatly increase the number of neurons involved in the loss of cell function.

It is believed that if one could rapidly increase the blood flow to the region, where the initial blockage occurred, the effects of the stroke could be substantially diminished. In many instances, mortality could be prevented. It is also of interest to be able to treat people who are susceptible to the formation of clots, particularly under conditions where the potential for clot formation is enhanced, such as operations.

It is not simply a matter of increasing the heart rate or blood flow to the heart since this may have only little or no effect on the amount of blood through the brain capillaries. Therefore, effects one may observe with blood vessels associated with other organs may not be translated to the effect one may anticipate in the case of stroke. Furthermore, there is substantial difficulty in being able to evaluate a drug as to its effectiveness in ameliorating the effects of stroke. Using individuals for various tests does not necessarily reflect the effectiveness of a drug, since a number of factors may come into play unrelated to the drug, but rather associated with holistic or placebo effects. There is thus a need for a carefully controlled test system for evaluating the efficacy of potential drugs for treating stroke.

RELEVANT LITERATURE

Guo Shi-kui et al., *Planta Medica* (1983) 47:89 reports the use of tetramethylpyrazine in the treatment of cardiovascular and cerebrovascular diseases. Ojewole, *Planta Medica* (1981) 42:223-228, reports the effects of tetramethylpyrazine on isolated atria of the guinea pig. Ojewole, *Planta Medica* (1981) 43:1-10 reports the use of tetramethylpyrazine in the blockade of adrenergic and cholinergic transmissions by tetramethylpyrazine. Xue-Zheng Dai and Bache, *J. of Cardiovascular Pharmacology* (1985) 7:841-849, reports the coronary and systemic chemodynamic effects of tetramethylpyrazine in the dog.

The following papers describe procedures for studying drugs and their effect on ischemic deficits with cats: Baskin and Hosobuchi *Lancet* (August 8, 1981) p.272-275, and Baskin et al., *Brain Research* (1984) 290:289-296.

Ohta et al., *Heterocycles* (1984) 22:2317-2321 describe tetraalkyl-substituted pyrazines, where the alkyl groups are from 1 to 3 carbon atoms.

SUMMARY OF THE INVENTION

Tetraalkyl-substituted pyrazines are infused over extended periods of time into a mammalian host to inhibit an increase in ischemia over the then existing ischemic state of the host. The presence of the pyrazine derivative reduces the observed ischemic deficits and/or improves survival as compared to a mammalian host who has received no treatment.

DESCRIPTION OF THE SPECIFIC EMBODIMENTS

A mammalian host subject to an increase in neuronal damage due to blood flow blockage in the brain is treated with a tetraalkyl-substituted pyrazine over an extended period of time, resulting in substantially reduced ischemic deficits. The method employs maintaining within a relatively narrow range an effective concentration of the pyrazine compound over an extended period of time prior to or during the onset of the stroke.

The compounds which are employed are tetra-C-substituted pyrazines, particularly alkyl of from one to three carbon atoms, more particularly straight chain alkyl, preferably symmetrically substituted, where the alkyl groups are methyl, ethyl, propyl-l, and propyl-2, particularly methyl. The compounds may be readily prepared as described by Ohta et al., *Heterocycles* (1984) 22:2317-2321.

The compounds may be formulated in a variety of ways and may be used by themselves or in conjunction with other drugs. The formulation will be in a physiologically acceptable medium, which should be readily acceptable as a medium for repetitive introduction or continuous introduction into the host. Convenient media include saline, phosphate buffered saline, lactated Ringer's solution, 5% dextrose in water, polyethyleneglycol and the like.

The concentration of the drug in the medium will generally be in the range of about 0.5% to 5%, more usually in the range of about 1% to 2%. The concentration may be in the upper portion of the range initially and then may be lowered as the drug is continuously administered. Usually, the concentration will not be diminished below the lower portion of the preferred range in the first 12, or even in the first 24 hours of treatment.

Where there has already been an onset of stroke, desirably, an initial bolus will be administered to the patient, which may be intraveneously administered, intraperitoneally, intraarterially, subcutaneously, intrathecally, or the like, preferably being administered in a manner in which the drug will be rapidly carried across the blood-brain barrier into the brain to initiate its effect. Therefore, it will be preferable to introduce the bolus into the vascular system. The same media which are used for the infusion may also be used for the bolus, although other media may be used as well, such as normal saline, ¼ normal saline, ½ normal saline, lactated Ringer's solution, 5% dextrose in water, and polyethyleneglycol. The concentration in the bolus will generally be from about 0.5% to 5%, more usually from about 1% to 2%.

Desirably, the bolus should be administered within a relatively short time after the stroke, conveniently within 12 hours, generally from about zero to eight hours, more usually from about zero to six hours.

After administration of the bolus, various means may be employed for maintaining a relatively constant concentration of the pyrazine in the patient. Most conveniently, an intravenous solution would be administered with the rate of infusion carefully controlled using an external flow-modulating device. A pump may be implanted in the patient, so as to continuously provide the desired level of drug. In these ways, one can be assured that the amount of drug is maintained at the desired level and one can take blood samples and monitor the amount of drug in the bloodstream. Various pumps are commercially available, such as the Alzet osmotic pump, model 2MLI, Alza Corp., Palo Alto, CA. Other methods which may be employed besides continuous infusion are repetitive injections in accordance with a pre-determined schedule, interrupted intravenous infusion, or the like.

The period for which drug is continuously or repetitively administered will generally be at least about three hours and not more than about twelve days, usually not more than about six days. Response may be observed within about 15 minutes and usually within about 48 hours, more usually within about 24 hours. Response is observed by an improvement in neurological function, such as improved movement. Also extended survival times are achieved.

The method employed for establishing the effectiveness of a drug in enhancing neurological function, improving survival, and reducing ischemic deficits from stroke is to use cats as the subject. It is found that cats do not have a single middle cerebral artery. Therefore, to simply occlude the middle cerebral artery is not sufficient. There is a rete of cerebral vessels in the cat or a number of different vessels that could come off from different areas to supply the particular area of the brain of interest. Thus, one could obtain variable results if one ignores the fact of the plurality of cerebral arteries.

The subject test method is described as follows.

Nine adult male cats of similar weight and age were selected for this study. Cats (4 kg, 1-2 years) were purchased and were appropriately vaccinated and conditioned for 30 days prior to their entry into the study. The cats were sedated with 50 mg of ketamine and 0.25 mg of atropine administered intramuscularly. Anesthesia was induced by first administering halothane by mask and then the trachea was intubated. The cat was allowed to breathe spontaneously. One million units of penicillin G was administered intramuscularly, and the cats were placed in a stereotaxic apparatus.

Transorbital occlusion of the right middle cerebral artery is performed using a modification of the technique first described in cats by O'Brien and Waltz. In brief, an incision is made in the superolateral aspect of the orbit, and using sharp dissection, the junction of the conjuctiva and the superior and interior orbital rims are exposed. Using a subperiosteal dissection, the conjunctiva is stripped from the orbit. Once hemostasis is obtained the globe is incised and the contents of the anterior and posterior chambers are evacuated, along with the lens. The collapsed globe is then dissected free back to the attachment of the extraocular muscles, which are coagulated with a Bovie electrocautery unit, and are removed. The orbit is systematically emptied of its contents until the optic nerve is exposed. Using a bipolar coagulating forceps, the optic nerve and the central retinal artery are coagulated and transected. The remaining contents of the orbit are then removed, exposing the optic strut.

Using an operating microscope from this point forth, the optic strut is drilled away, along with bone superior and lateral to the superior orbital fissure. Using a high speed drill, the bone is removed until only a thin rim remains. A small curette is then used to remove the bone, exposing the underlying dura. The dura is then opened by sharp dissection, and its free edges coagulated. This exposes the underlying brain and subarachnoid space.

Using a microdissector, the subarachnoid space is opened and cerebrospinal fluid is drained. After drainage, the brain is relaxed and drops away from the surgical field. The internal carotid artery is then identified and traced medially until its branch point into the middle cerebral and anterior cerebral arteries. The arachnoid is dissected free from the vessels and the middle cerebral artery is then coagulated at its takeoff from the internal carotid and transected using microscissors. All perforating vessels within 2 mm of either direction from the middle cerebral takeoff are also coagulated and transected. Hemostasis is obtained, and the orbit is then filled with methylmethacrylate. The orbit is then sutured using a 3-0 Proline.

The cat is then allowed to awaken, and evaluated one hour later using a 40 point scale to grade gait, forepaw and hindpaw motor and sensory function, circling, level of consciousness, and pupillary responses to light.

Table A

40 Point Neurological Assessment Scale

Neurological Assessment
A. Motor Function
  10 - Cat walks with normal gait - no neurological deficit
  9 - Cat walks normally placing all paws correctly >80% of the time.
  8 - Cat walks with abnormal gait, mild hemiparesis, places all paws at least 50% of the time, may stumble or slide.
  7 - Cat lifts himself to walk for short distance (<5 steps).
A. Motor Function (continued)
  6 - Cat barely walks with moderate hemiparesis, gets body off ground for brief periods, momentary weight bearing on paws with forward movement.
  5 - Cat unable to walk with moderate hemiparesis, momentary weight bearing on paws, but not on footpad, to produce a slight forward movement.
  4 - Cat unable to walk with moderate to severe hemiparesis, momentary weight bearing on paws but does not produce forward movement.
  3 - Cat unable to walk with severe hemiparesis, there is movement in limbs but the animal does not bear weight or produce forward motion.
  2 - Cat unable to walk with extremely severe hemiparesis, there is a flicker of movement in the limbs.
  1 - Cat unable to walk with hemiplegia.
B. Forepaw
  7 - Normal function.
  6 - Paw weight bearing and placed normally >50% of the time, paw may slide out or rest on metacarpals.
  5 - Paw weight bearing but not placed normally, placed on metacarpal of paw.
  4 - Paw weight bearing for a brief moment, then slips.

3 - Paw moves well but not weight bearing.
    2 - Paw barely moves.
    1 - Paw does not move.
C. Hindpaw
    6 - Normal function.
    5 - Paw is weight bearing and placed correctly, but may slide out.
    4 - Paw weight bearing for a brief moment, slips out.
    3 - Paw moves well but not weight bearing.
    2 - Paw barely moves.
    1 - Paw does not move.
D. Circling
    5 - Normal, does not circle.
    4 - Intermittent, circles then walks in straight line.
    3 - Broad circling behavior.
D. Circling (continued)
    2 - Variable circle behavior, tight to broad circles.
    1 - Tight circling behavior.
    0 - Unable to assess because cat does not walk.
E. Sensory - Forepaw
    4 - Normal reaction - immediate withdrawal from stimulation.
    3 - Cat withdraws paw but response is slow.
    2 - Cat responds with a small twitch of paw.
    1 - Cat does not respond to stimulation.
F. Sensory - Hindpaw
    4 - Normal reaction - immediate withdrawl from stimulation.
    3 - Cat withdraws paw but response is slow.
    2 - Cat responds with a small twitch of paw.
    1 - Cat does not respond to stimulation.
G. Level of Consciousness
    4 - Cat normal, alert and awake.
    3 - Cat is awake but not alert, does not respond to a hand clap or loud noise; drowsy.
    2 - Cat not alert or awake, needs a lot of stimulation to produce a response; stuporous.
    1 - Cat comatose.

Neurologic function is assessed by two individuals and a video record is made of the cat's performance. At either one hour after stroke (five cats), two hours after stroke (one cat), four hours after stroke (two cats), or six hours after stroke (one cat), the cat is then anesthetized using a mixture of halothane and oxygen administered by mask. A cut-down is performed in the right femoral region exposing the femoral artery and femoral vein. An intravenous injection is made in the forepaw of the animal using the drug, and then an ALZA 2MLI osmotic pump (ALZET osmotic pump, model 2MLI, manufactured by the ALZA Corporation, Palo Alto, California) is implanted in the femoral region, connected to a polyethylene tubing inserted into the femoral vein using a femoral vein cut-down technique. The pump is designed to deliver 10 ml per hour of the drug.

The cat is then allowed to awaken and is evaluated over a six hour period at 15 minute intervals. Evaluations include general observation, rating according to the 40 point neurological scale, and video filming.

Neurological assessments and filmings were then performed daily for as long as the cats were alive, or until seven days after occlusion, at which time all were sacrificed. The cats were housed in metabolic cages in a constant temperature and humidity environment, and were observed frequently by laboratory and veterinary staff. One million units of penicillin G was administered intramuscularly daily along with subcutaneous injections of Lactated Ringers solution calculated to provide daily adequate fluid maintenance. Once a cat began to eat or drink, subcutaneous fluids were discontinued.

If a cat was found dead, a craniectomy was performed, the brain removed, and serial coronal sections were made, including sections at the level of the optic chiasm and the mammillary bodies. At the end of seven days, all surviving cats were sacrificed, the brains removed and slices prepared. The slices were incubated in a 2% solution 2,3,5,-triphenyltetrazolium chloride (TTC) for 25 minutes according to the method of Han, et al. in Rivich, M. and Huntig, H.I. (eds.): Cerebrovascular Diseases Research (Princeton) 13th Conference N.Y.: Raven Press, 1983, pp 409–419. TTC solution has been used extensively to demonstrate the presence and extent of acute myocardial infarcts, and gives a vivid indication of cerebral infarction in the acute stage. The reaction product of TTC in viable tissue is a deep red formazan that stains normal gray matter, whereas normal white matter stains with less intensity. Infarcted tissue does not stain.

Color slides were then made of the stained brain slices. Tracings were made of the entire affected hemisphere and the infarcted area from projected images of the slide. Using a digitizer, the percentage of infarcted tissue relative to the entire hemisphere was obtained for sections both at the optic chiasm and at the mammillary bodies. The individual sections were then formalin fixed, sectioned sagittally in the midline, and the hemisphere with the infarct was weighed. After weighing, the infarcted tissue was excised and the section was weighed again. The percent of infarct volume relative to the entire hemisphere was then calculated by summing the results of the subtraction of the weight of each section after the infarct was excised from the weight prior to excision, and dividing this value by the sum of the weight of the individual sections prior to excision.

Several variables were investigated in this study. First, the effect of administration of drug either intravenously or intraperitoneally was investigated, as well as whether continuous infusion needed to be via an intravenous or subcutaneous route. The time frame from stroke to treatment also was varied, from one hour (five animals), two hours (one animal), four hours (two animals), or six hours (one animal).

In a study following the above procedure, nine cats were treated employing saline as the infusion medium. The following table indicates the results.

TABLE I

Summary of Pilot Study Data
RESULTS

| Cat # | Time From Stroke to To Treatment | Neurologic Function Pretreatment | Route of Initial Admin. | Route of Pump Implant. | Time to 1st Response From Admin. of Drug | Time of Best Response | Survival |
|---|---|---|---|---|---|---|---|
| 1 | 1 hour | severe | I.V. | I.V. | 20 minutes | 2 hours | 1 week |
| 2 | 1 hour | severe | I.V. | I.V. | 1 hour | 2 days | 4 days |
| 3 | 1 hour | severe | Dbl. I.V. | I.V. | 40 minutes | 1.5 hours | 2 days |
| 4 | 1 hour | severe | Intraperi- | Subcu- | next day | next day | 1 week |

TABLE I-continued

Summary of Pilot Study Data
RESULTS

| Cat # | Time From Stroke to To Treatment | Neurologic Function Pretreatment | Route of Initial Admin. | Route of Pump Implant. | Time to 1st Response From Admin. of Drug | Time of Best Response | Survival |
|---|---|---|---|---|---|---|---|
| 5 | 1 hour | moderate | toneally I.V. | taneously Subcutaneously | 1 hour | 2 hours | 1 day |
| 6 | 2 hours | moderate to severe | I.V. | I.V. | 2 hours | 2 hours | 2 days |
| 7 | 4 hours | moderate | I.V. | I.V. | 40 minutes | 4 hours | 2 days |
| 8 | 4 hours | severe | I.V. | I.V. | 30 minutes | 4 hours | 2 days |
| 9 | 6 hours | mild | I.V. | I.V. | 4 hours | next day | 7 days |

The above data show that in all cats tested with tetramethylpyrazine with a bolus dosage of 2 cc of 2% solution with a flow rate of 10 μl per hour, significant improvement was seen. All animals showed significant improvement in neurologic function, ranging from as early as 20 minutes after injection until the following morning. No cat which received the drug failed to improve in function regardless of the severity of the initial stroke. It also appears that the response to therapy was effective for as long as 6 hours after production of the stroke. This is consistent with the concept that cerebral ischemia is reversible if treated within the first 6 hours.

So far as survival time, the results are somewhat more equivocal particularly, since in cats 2, 6, and 7, the pump tubing kinked at about the time the animal died. This was determined by weighing the pump before and at the time of death and calculating how long the pump had been able to pump until the tubing kinked. In cat 2, the pump closed off somewhere in the morning of the fourth day, with death following later that day. Cat 3 died two days later of an acute subdural hematoma, which could be explained by an overdose of the drug, as the cat was given a dose twice when the first dose infiltrated through his vein.

Infarct size data revealed an average cross-sectional area of infarction at the level of the optic chiasm of 21%. Comparing these results to saline treated controls from previous experiments using the same technique, the experience showed there was no improvement in neurologic function, 100% mortality occurred within 24 hours, and a 60% infarct size considering cross-sectional area of infarct at the level of optic chiasm.

The above results demonstrate that the tetraalkylpyrazines are effective drugs in the treatment of stroke, improve survival, minimizing ischemic deficits, enhancing neurologic function, which apparently relates to the improved blood flow in the region of the infarct within a short time after the stroke has occurred. Thus, patients will suffer less neurological dysfunction, recover more rapidly, and have a lower incidence of permanent damage, and more often survive.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for diminishing the ischemic deficits as a result of stroke and enhancing survival, said method comprising:
   administering to a mammalian host as a single bolus an effective amount of a tetramethylpyrazine to enhance the blood flow to the brain of said host; and
   continuing administration of said tetramethylpyrazine for at least one additional hour by continuous infusion or repetitive administration while maintaining the blood level at at least an effective amount of tetramethylpyrazine to maintain an enhanced blood flow to the brain.

2. A method according to claim 1, wherein said administering is prior to a stroke.

3. A method according to claim 1, wherein said continuing administration is by means of a pump or by continuous intravenous infusion.

4. A method for diminishing the ischemic deficits as a result of stroke, said method comprising:
   administering to a mammalian host suffering from stroke within six hours of the onset of said stroke as a single bolus an effective amount of tetramethylpyrazine to enhance the blood flow to the brain of said host; and
   continuing administration of said tetramethylpyrazine for at least six additional hours by continuous infusion while maintaining the blood level at at least an effective amount of tetramethylpyrazine to maintain an enhanced blood flow to the brain.

5. A method according to claim 4, wherein said continuing administration is by means of a pump or by means of continuous intravenous infusion.

6. A continuous infusion apparatus comprising a physiologically acceptable solution of a tetramethylpyrazine at a concentration to enhance blood flow in a mammalian host upon infusion into said host.

* * * * *